US00PP16801P2

(12) United States Plant Patent

Taliaferro et al.

(10) Patent No.: US PP16,801 P2

(45) Date of Patent: Jul. 11, 2006

(54) PATRIOT TURF BERMUDAGRASS

(50) Latin Name: ***Cynodon dactylon* var. *dactylon*×*C. transvaalensis***
Varietal Denomination: Patriot

(75) Inventors: Charles M. Taliaferro, Stillwater, OK (US); Dennis L. Martin, Stillwater, OK (US); Jeffrey A. Anderson, Stillwater, OK (US); Michael P. Anderson, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 1 day.

(21) Appl. No.: 10/873,809

(22) Filed: Jun. 22, 2004

(51) Int. Cl.
*A01H 5/00* (2006.01)

(52) U.S. Cl. ..... Plt./389

(58) Field of Classification Search ..... Plt./389
See application file for complete search history.

(56) References Cited

PUBLICATIONS

United States Department of Agriculture, Agricultural Research Service, National Bermudagrass Test Final Report 1997–2001, *NTEP* No. 02–7.

Anderson et al., Longer Exposure Durations Increase Freeze Damage to Turf Bermudagrasses, 2003, *Crop Sci.*, vol. 43, pp 973–977.

Anonymous, Shanghai Bermudagrass—The True Blue-Green Winter Hardy Grass for the South, Access Jul. 8, 2003, *SuperSod, a division of Patten Seed Company*, published on world wide web at http://www.pattenseed.com/sod–bgsh.html.

Hanna et al., Registration of 'Tifton 10' Bermudagrass, 1990, *Crop Sci.*, vol. 30(6), pp 1355–1356.

Landry, Bermudagrass Lawn Management, 1996, *Educational Support Services of the Cooperative Extension Service of The University of Georgia*, Circular 837.

*Primary Examiner*—Anne Marie Grunberg
*Assistant Examiner*—Annette H Para
(74) *Attorney, Agent, or Firm*—Fellers, Snider, Blankenship, Bailey & Tippens, P.C.

(57) ABSTRACT

'Patriot' is an improved clonal turf bermudagrass cultivar suitable for many applications including golf course fairways and tees athletic fields, home and commercial landscape sites, and parks and playgrounds. It is a tetraploid (2n=4x=36 chromosomes) interspecific $F_1$ hybrid from a cross of *Cynodon dactylon* by *C. transvaalensis* characterized by dark blue-green color, vigorous growth, good winter hardiness, and good turf quality.

8 Drawing Sheets

BACKGROUND OF THE INVENTION

1. Field of the Invention

'Patriot' bermudagrass is a clonally propagated $F_1$ hybrid plant from a cross of *Cynodon dactylon* var. *dactylon* by *C. transvaalensis*. The cultivar will be marketed as Certified class sod and/or Certified class sprigs.

Background of the Invention:

The maternal parent of 'Patriot' was 'Tifton 10' bermudagrass, *Cynodon dactylon* var. *dactylon*. The pollen parent of 'Patriot' was a selected plant of *Cynodon transvaalensis* designated by its field nursery location identity as 4200 TN 26-8. 'Tifton 10' is a commercial cultivar that differs from most *C. dactylon* plants in having 54 chromosomes (hexaploid; 2n=6x=54) compared to the usual 36 chromosomes (tetraploid; 2n=4x=36) and having a darker green foliage color (Hanna, et al., 1990). The *C. transvaalensis* pollen parent has 18 chromosomes (diploid; 2n=2x=18). 'Patriot' is a tetraploid with 2n=4x=36 chromosomes, presumably having inherited 27 chromosomes (3 genomes) from 'Tifton 10' and 9 chromosomes (1 genome) from the *C. transvaalensis* parent.

The cross between 'Tifton 10' and *C. transvaalensis* "4200 TN 26-8" was made in 1992. Seeds from this cross and crosses between other parent plants were germinated in late winter 1993 and the seedlings individually planted in greenhouse pots. The potted plants were transplanted to a field screening nursery in spring 1993 as spaced (3 meter centers) plants. 'Patriot' was first vegetatively propagated in late 1994. The vegatative propagation occurred in a greenhouse on the Agronomy Farm, Oklahoma State University and was selected in late 1994 for advancement to more comprehensive testing including testing in replicated experiments through time and space to measure adaptation and performance characteristics. At the time of its first selection in 1994 it was identified as "OKC 18-4" and evaluated under this designation. 'Patriot' has been clonally propagated through many generations since 1994 without any indication of genetic change. Advanced generation clonal plants appear identical to the original plant in morphological phenotype and in genetic characteristics that have been measured.

SUMMARY OF THE INVENTION

'Patriot' bermudagrass produces a high quality turf suitable for most turf applications including golf course fairways and tees, home lawns, commercial lawns, playgrounds, parks, and athletic fields. 'Patriot' produces a dense, dark-green turf of high visual quality. It has medium-fine texture, grows vigorously, and has good cold hardiness. These characteristics make it especially useful in climatic regions representing zones of transition between cool- and warm-season turfgrass species. 'Patriot' is an $F_1$ hybrid of the cross 'Tifton 10' by *C. transvaalensis* "4200 TN 26-8". It has 2n=4x=36 chromosomes having inherited 27 chromosomes (3 genomes) from 'Tifton 10' and 9 chromosomes (1 genome) from *C. transvaalensis*. 'Patriot' is highly sterile and is propagated asexually by sprigs and sod. 'Patriot' can be distinguished from other turf bermudagrass cultivars by morphological and/or genetic characteristics outlined herein.

DETAILED BOTANICAL DESCRIPTION

Figure 1:
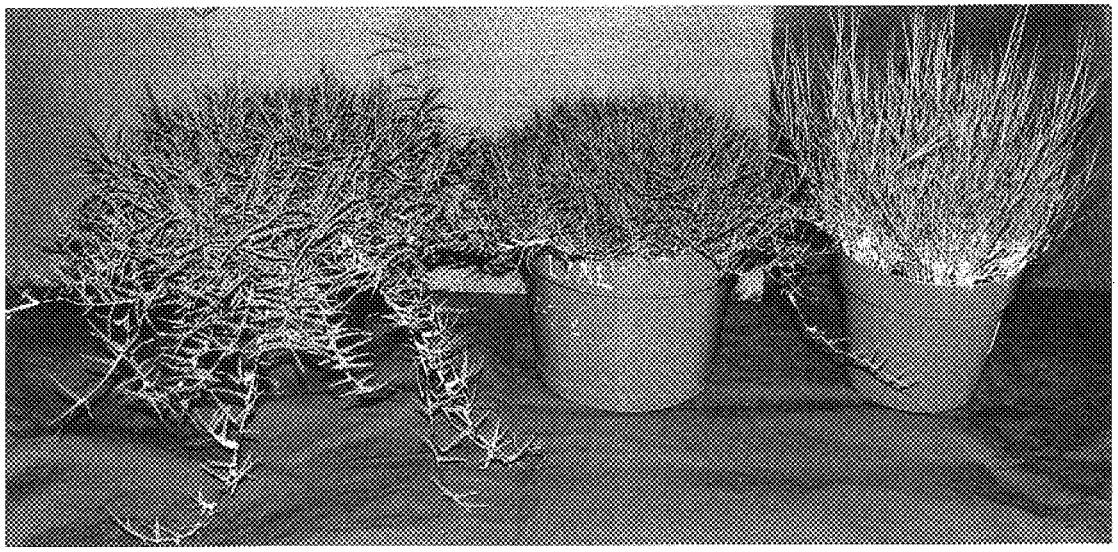
FIG. 1 is a photograph of five-week old growth of 'Tifton 10' (left), 'Patriot' (center), and *C. transvaalensis* "4200 TN 26-8" (right). The intermediate size and texture of 'Patriot' relative to the parents are illustrated.
Figure 2:
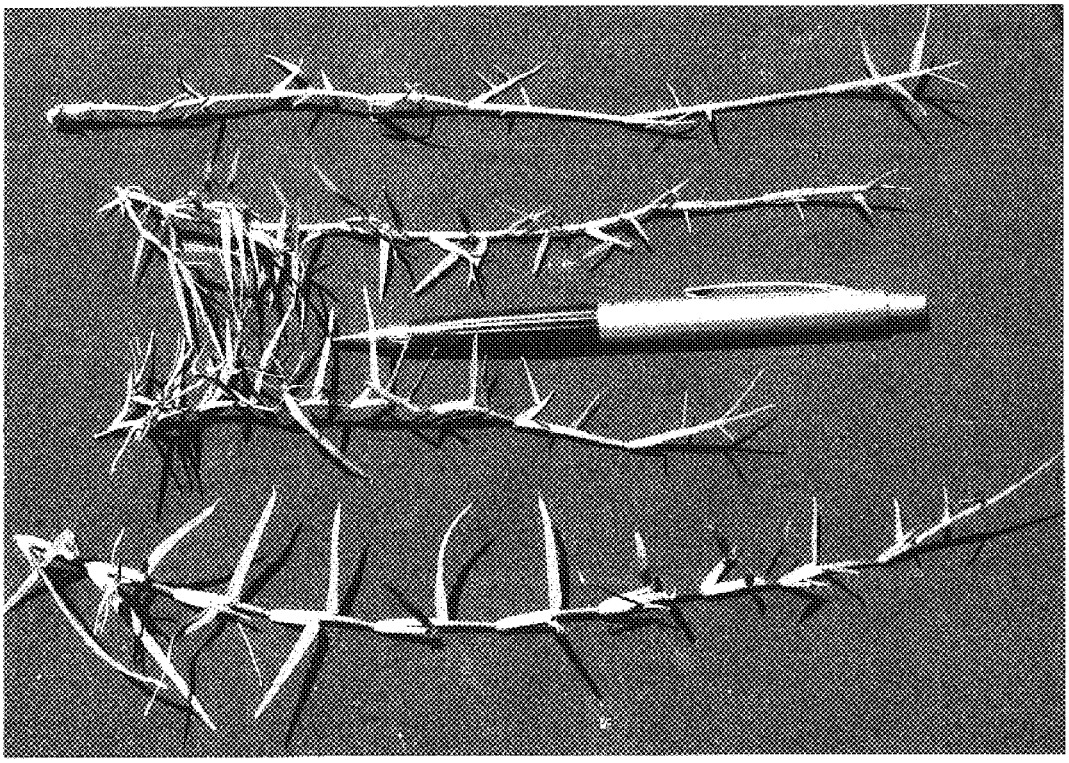
FIG. 2 illustrates stolons of 'Tifton 10' (bottom), 'Patriot' (second from bottom), 'U-3' (third from bottom), and 'Quicksand' (top). Stolons were taken from five-week old growth of potted plants in the greenhouse. The relative length and diameter of internodes is illustrated as are the relative length and width of leaves.
Figure 3:
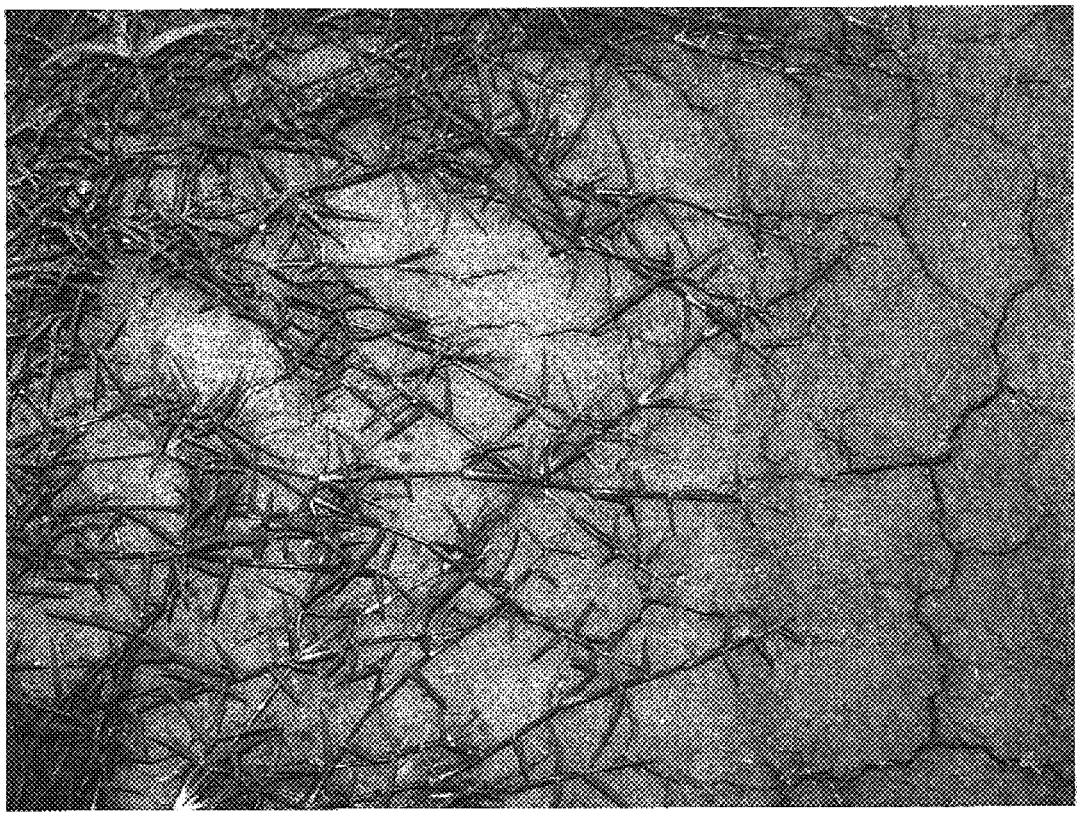
FIG. 3 illustrates laterally growing stolons of 'Patriot' during stand establishment. The photograph was taken in early October showing the response of 'Patriot' to cool temperatures in production of anthocyanin pigmentation.
Figure 4:
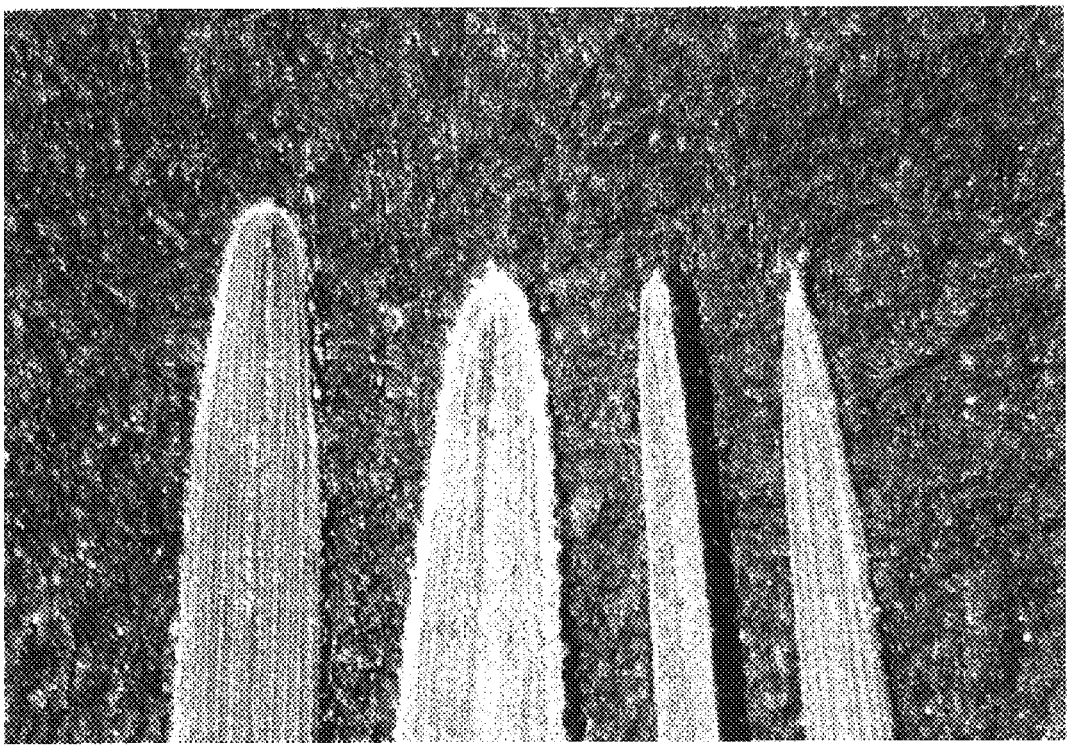
FIG. 4 illustrates leaf tips of 'Patriot' (left), 'Tifton 10' (second from left), *C. transvaalensis* "4200 TN 26-8" (third from left), and 'U-3' (right). Leaf tips of 'Patriot' and 'Tifton 10' leaf tips tend to be more oval and less pointed than typically found in bermudagrass.
Figure 5:
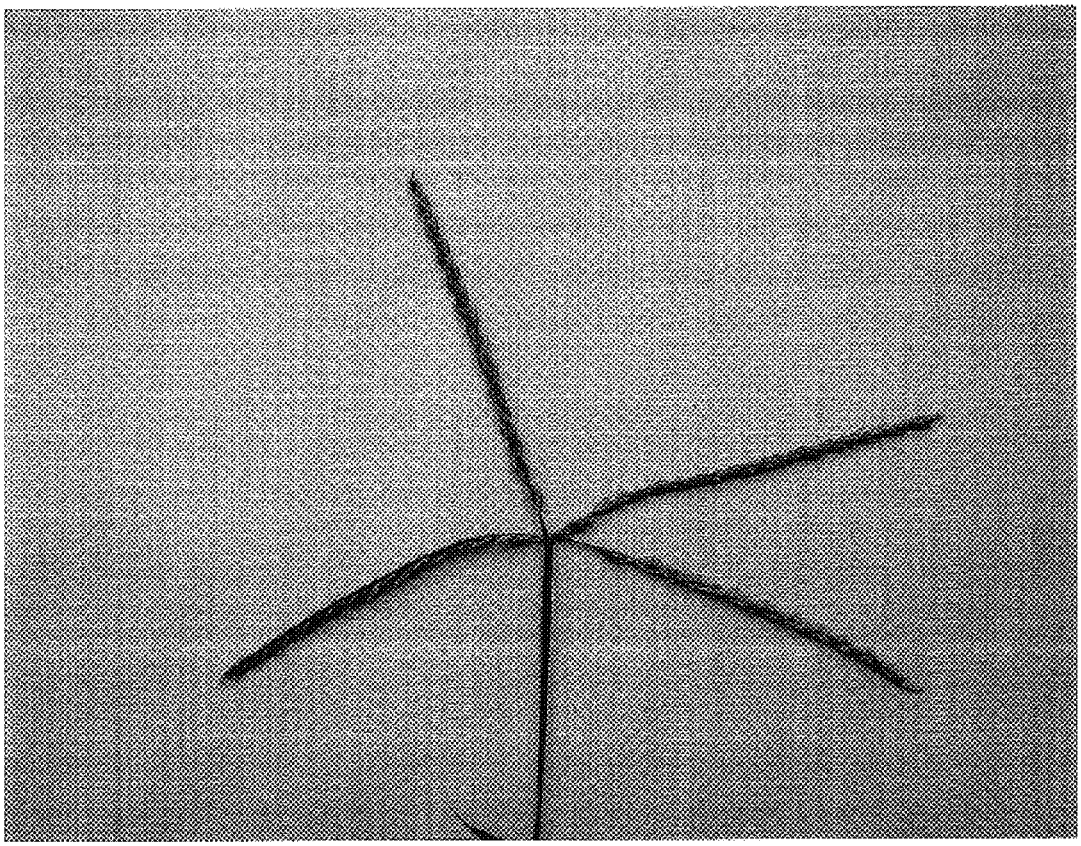
FIG. 5 illustrates a typical inflorescence of 'Patriot' with four racemes typically varying in length from 2.5 to 3.5 cm.

'Patriot' experimental name "OKC 18-4") is a distinct cultivar of *Cynodon* from the interspecific cross of *C. dactylon* Pers. cv. 'Tifton 10' and *C. transvaalensis* Burtt-Davy cv. '4200 TN 26-8'. It was developed and vegetatively propagated by the Oklahoma Agricultural Experiment Station, Stillwater, Okla. Identifying morphological characteristics of 'Patriot' are its dark green color, strong anthocyanin pigmentation of stolon internodes during periods of cool temperatures, and high shoot density. It is intermediate to its parents in plant size and texture as illustrated in FIG. 1. 'Patriot' has finer texture than 'Tifton 10', 'U-3', and 'Quickstand' as illustrated in FIG. 2 by the relative diameter and length of stolons and stolon internodes. 'Patriot' is a stoloniferous sward-forming perennial with slender underground rhizomes; surface stolons are slender attaining a maximum diameter of approximately 1 mm, and a maximum internode length of approximately 6 cm. During establishment under good growing conditions stolons may attain a length of approximately 70 cm (FIG. 3). Shoot numbers emanating from nodes of stoloniferous runners range from 2 to 5 and average 3.0. Culms are slender varying in height on unmowed swards from about 10 to 25 cm. Culm density is high producing a dense sward (sod). Culm leaves are flat, glabrous on the abaxial and adaxial surfaces, and slightly serrate on the edges. Culm leaves emanating from the last visible node below the apex of shoots vary in width at their base from 2 to 4 mm and range in length from about 25 to 38 mm. The leaf tips resemble the Tifton 10 parent and are more rounded that is typical for *Cynodon* plants (FIG. 4) The ligule is a membranous rim about 0.2 mm long with very short hairs on the edge except at the outer edges where a tuft of much longer hairs grow. Leaf sheaths are glabrous. Inflorescence is a single whorl of 2 to 5, usually 3 or 4, racemes averaging 33 mm in length (FIG. 5). Racemes contain on average 25 spikelets spaced 2 mm apart and 2 mm in length. The lower and upper glumes are approximately ½ and ¾ the length of the spikelet.

'Patriot' was evaluated under the experimental name 'OKC 18-4' in the National Turf Evaluation Program (NTEP) bermudagrass test conducted at 21 locations from 1997 through 2001. This multi-environment testing provided the most definitive data on the performance characteristics of 'Patriot' relative to other major commercial clonal turf bermudagrass cultivars. The trademarked cultivar 'Shanghai' in this test is indicated by descriptions published by the Patton Seed Co. (2003) and Landry (2003) to be the same as 'Tifton-10'.

Figure 6:
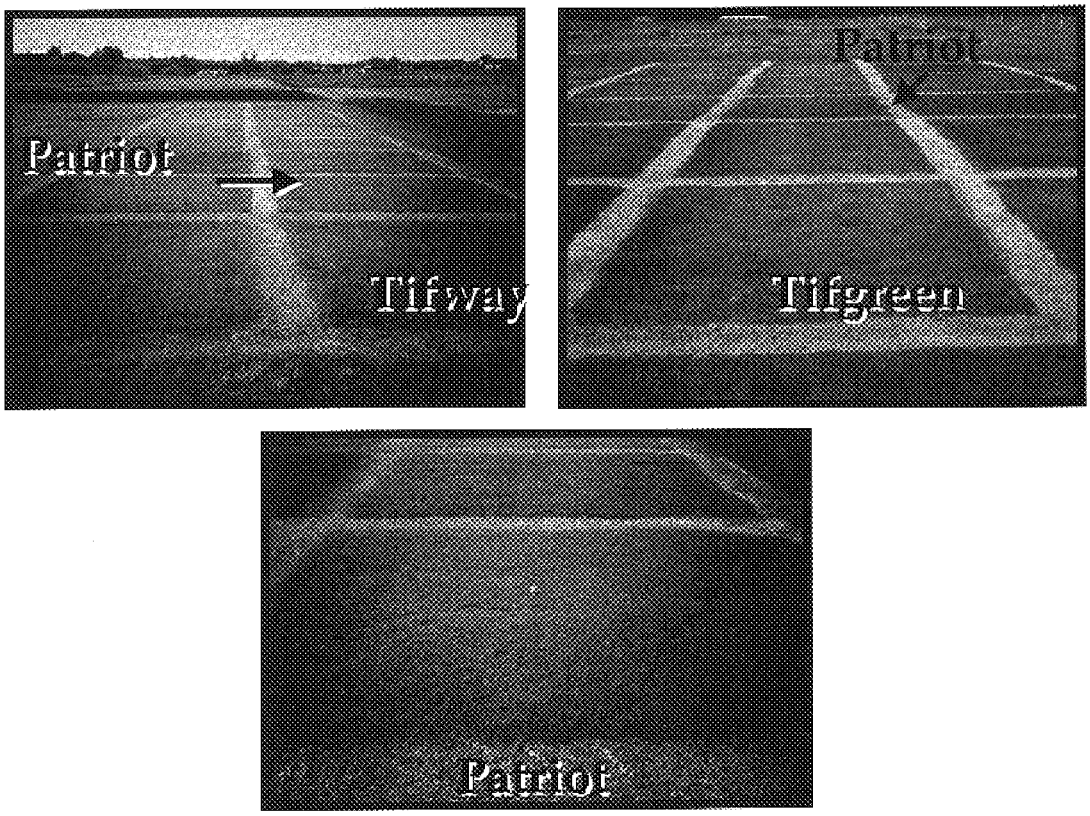
FIG. 6 are photographs of 'Patriot', 'Tifway', and 'Tifgreen' mowed twice weekly at 19 mm (3.4 inch) height. A) 'Patriot' and Tifway, B) 'Patriot' and Tifgreen, and C) close-up of 'Patriot'.

'Patriot' produces a high quality turf surface as indicated by visual ratings of turf quality (Table 1, FIG. 6). Under management schedule "A" ½ to ¾ in. mowing height), the mean turf quality rating of 'Patriot' (6.1) was less than that of Tifway (6.4) and Tifsport (6.5), equal to that of CN 2-9, and greater than all other cultivars, including 'Shanghai'. Under management schedule "B" ¾ to 1 inch mowing height), the mean turf quality rating of 'Patriot' (6.6) was significantly higher than those of all cultivars except 'Midlawn'.

'Patriot' is relatively stable in turfgrass quality performance across environments (Table 2). It was lowest of all clonal varieties in sum-of-ranks across locations and finished in the top 25% of all entries in 65% of the locations.

'Patriot' has not shown high susceptibility to the major disease or insect pests of turf bermudagrass in the northern half of geographic region of bermudagrass use in the U.S. where it is expected to primarily be used. Spring dead spot disease caused by *Ophiosphaerella herpotricha* is the most serious disease of turf bermudagrass in the upper south of the U.S. 'Patriot' was evaluated for response to spring dead spot disease in a controlled test at Stillwater, Okla. during 2000 through 2002. Replicated plots were inoculated in September 1997 with *Ophiosphaerella herpotricha*. Measurements of the size of necrotic patches indicated 'Patriot' to have good tolerance to the disease (Table 10), much higher than very susceptible cultivars such as Tifway. 'Patriot' has exhibited very little leaf disease indicating it to be highly resistant to such disease caused by *Bipolaris cynodontis* and other dematiaceous fungal pathogens. 'Patriot' has good resistance to the bermudagrass stunt mite,

*Aceria neocynodonis*, as indicated by minimal infestation when grown in field nurseries with other bermudagrasses that exhibited severe infestation. 'Patriot' has not been evaluated for response to fall armyworm, *Spodoptera frugiperda*, black cutworm, *Agriotis ipsilon*, or sod webworm, *Herpetogramma phaeopteralis*, all pests of bermudagrass. However, no sigificant injury was observed due to these pests during the time 'Patriot' was under evaluation.

Mean genetic color ratings of 'Patriot' were the same as those of Shanghai and CN 2-9 and greater than all other clonal cultivars (Table 3). 'Patriot' has nearly the same dark blue-green color of Tifton-10 (FIG. 1).

'Patriot' bermudagrass fertilized monthly during the growing season with nitrogen at rates of 1.0 to 1.5 Lbs. N/1000 $ft^2$ has the following color scale ratings using Munsell® Color Charts (Munsell Color, GretabMacbeth, LLC, 617 Little Britain Road, New Windsor, N.Y. 12553) for Plant Tissues.

1. 'Patriot' produces leaves of dark green color [7.5 GY (4/4 to 4/6)].
2. 'Patriot' produces leaf sheaths that vary in color from green [7.5 GY. (6/60to 6/8)] to dark purple [10RP (2/4 to 3/4)]. The purple anthocyanin pigmentation varies with age of the sheaths and with environmental conditions, being more pronounced in older tissues and when the plant is subjected to cool termperatures. However, anthocyanin pigmentation is usually present in leaf sheaths of 'Patriot' throughout the growing season, with the presence and intensity the pigmentation tending to be greater in leaf sheaths emanating from stolons compared to leaf sheaths of upright shoots. Pigmentation usually first develops at the base of the sheath and may ultimately occur throughout the sheath.
3. 'Patriot' produces internodes that vary in color from light green [10Y (5/4 to 6/4)] to dark purple [(10RP (2/4 to 3/4)]. As in the case of leaf sheaths, anthocyanin pigmentation in internodes varies with age of tissue and environmental conditions in internodes as in leaves. Pigmentation tends to be more pronounced in older tissues and when plants are subjected to cool conditions. The presence and intensity of pigmentation tends to be greater in internodes emanating from stolons compared to upright shoots.
4. 'Patriot' bears inflorescences of light green color [2GY (6/6 to 6/8)]. At maturity the inflorescences are straw colored [2.5YG (6/4/ to 7/4)].

Mean leaf texture of 'Patriot' was rated equal to Midlawn and CN 2-9, finer than Shanghai, and coarser than other clonal cultivars (Table 4). 'Patriot' has distinctly finer leaf texture than Tifton-10 (FIG. 1).

Mean stand density (Table 5) and mean percent living ground cover (Table 6) of 'Patriot' as indicated by ratings are greatest during summer months and on a par with other clonal cultivars throughout the growing season.

Figure 7:
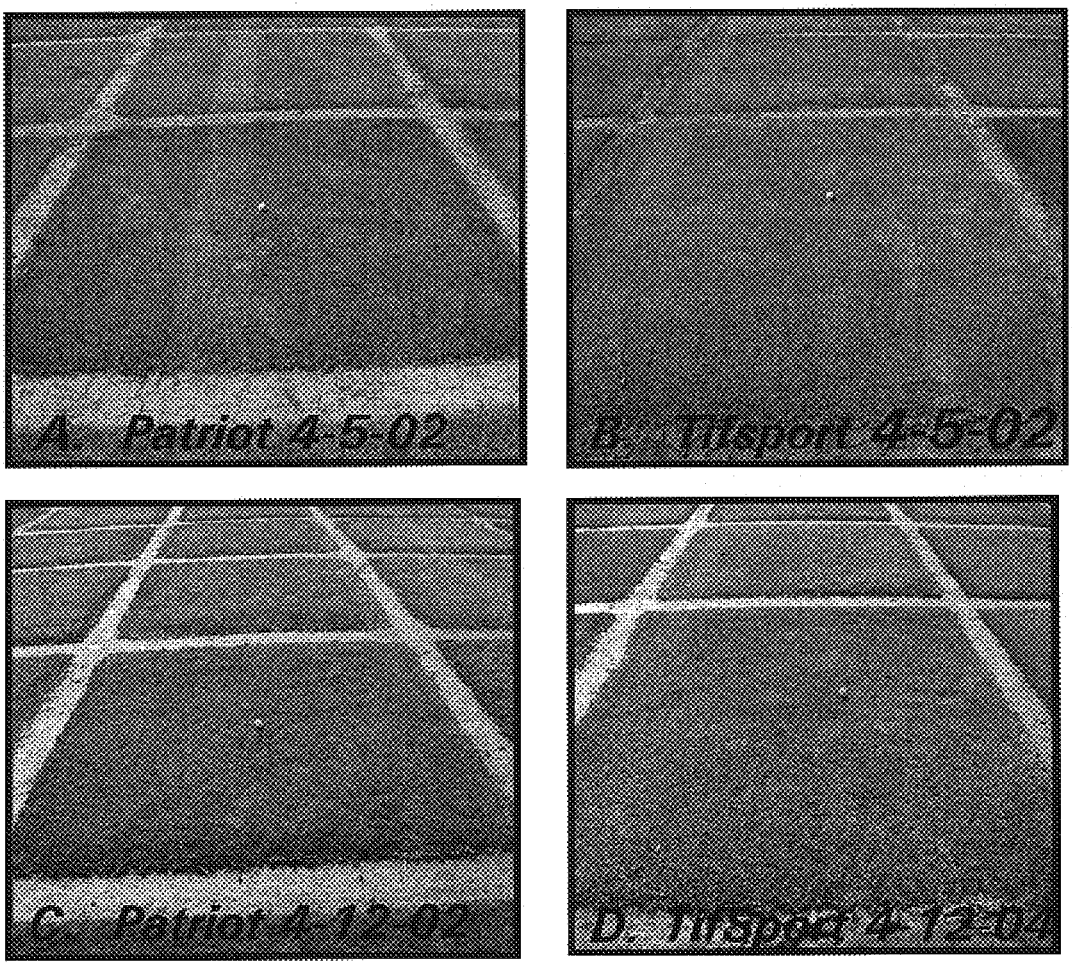
FIG. 7 are photographs of field plots of 'Patriot' (A & C) and 'Tifsport' (B & D) at Stillwater, Okla. on Apr. 5, 2002 and Apr. 12, 2002, demonstrating the typically earlier growth (green up) of 'Patriot' relative to Tifsport.

'Patriot' has good winter hardiness relative to other turf bermudagrass cultivars as indicated by winter injury ratings at Wichita, Kans. (Table 7) and laboratory measure of response to low freezing temperatures (Table 8). Its good low temperature tolerance reduces risk of winter injury relative to less winter hardy cultivars when grown in colder climatic regions where bermudagrass is used. The earlier growth of 'Patriot' relative to 'TifSport' at Stillwater, Okla. (36.06° N. Latitude; 9797.03 w. Longitude) is illustrated in FIG. 7.

'Patriot' has vigorous growth relative to other clonal cultivars as indicated by its spread during establishment at Fayetteville, Ark., Griffin, Ga., Lexington, Ky. and Starkville, Miss. (Table 9). The rate of spread during establishment of 'Patriot' and its growth potential are similar to Tifton 10 (Shanghai) although it has smaller plant size (texture). Ratings of seedhead abundance relative to other clonal cultivars may be found in Table 9a.

Figure 8:
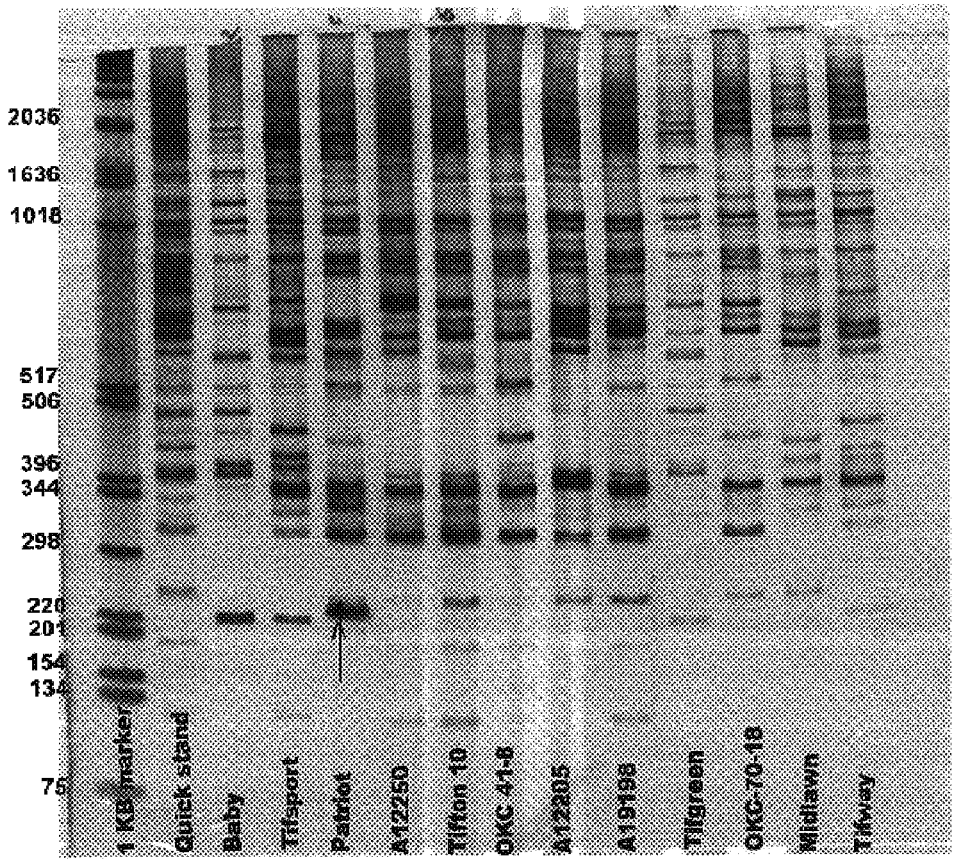
FIG. 8 illustrates the DNA profile of 'Patriot' and 12 other clonal turf bermudagrass cultivars using DAF (DNA amplification fingerprinting) primer 9111 (sequence GAAACGCC). The numbers on the Y axis indicate numbers of base pairs of nucelotides. The arrow points to a prominent band at the 220 bp region that is unique to 'Patriot' among these cultivars.

'Patriot' can be distinguished from other cultivars by DNA profiling. FIG. 8 shows a DAF (DNA Amplification Fingerprinting) profile using DAF primer 9111. The arrow points to a band at the 220 base pair region that is unique to 'Patriot' among the included cultivars. Other band differences also exist between 'Patriot' and the other cultivars in this profile.

The nuceotide sequence of DAF primer 9111 is 'GAAACGCC' (SEQ ID NO: 1). DAF primer 9111 was obtained from Integrated DNA Technologies, Inc., 1710 Commercial Park, Coralville, Iowa 52241.

TABLE 1

Mean turfgrass quality ratings[1] of 'Patriot' and eight other cultivars in the 1997 National Turf Evaluation Program bermudagrass test.[2]

| | Maintenance Schedule[3] | |
|---|---|---|
| Cultivar | "A" | "B" |
| Cardinal | 5.4 | 5.7 |
| CN2-9 | 6.1 | 5.8 |
| Midlawn | 5.8 | 6.5 |
| Mini-Verde | 5.6 | 5.1 |
| Patriot | 6.1 | 6.6 |
| Shanghai | 5.6 | 6.1 |
| Tifsport | 6.5 | 6.1 |
| Tifway | 6.4 | 6.2 |
| Tifgreen | 6.1 | 6.3 |
| 5% LSD | 0.2 | 0.2 |
| CV (%) | 15.8 | 14.2 |

[1]Based on a visual rating scale of 1 to 9 with 1 being poorest and 9 representing ideal turf.
[2]Means over years 1997 through 2001.
[3]Schedule "A": mowing height = ½ to ¾ inch, ¾ to 1 Lb. N/100 $ft^2$/growing month, irrigation to prevent visual drought stress, mowed 3 to 5 times/month. Schedule "B": mowing height = ¾ to 1 inch, ½ to ¾ Lb. N/1000 $ft^2$/growing month, irrigation to prevent dormancy, mowed 1 to 2 times/week. Schedule "A" conducted at nine locations; Schedule "B" conducted at 11 locations.

TABLE 2

Summary of turfgrass quality ratings for 'Patriot' and eight other cultivars in the 1997 National Turfgrass Evaluation Program bermudagrass test.

| | All locations | | Statistics for all locations | |
|---|---|---|---|---|
| Cultivar | Mean[1] | Rank[2] | Sum of Ranks[3] | Rank[4] |
| Clonal Cultivars | | | | |
| Cardinal | 5.5 | 13 | 327 | 15 |
| CN 2-9 | 5.9 | 9 | 213 | 10 |
| Midlawn | 6.1 | 7 | 156 | 7 |
| Mini-Verde | 5.4 | 14 | 312 | 13 |
| Patriot | 6.3 | 4 | 112 | 2 |
| Shanghai | 5.9 | 10 | 190 | 9 |
| Tifgreen | 6.2 | 6 | 136 | 6 |
| Tifsport | 6.4 | 2 | 125 | 4 |
| Tifway | 6.3 | 3 | 126 | 5 |

TABLE 2-continued

Summary of turfgrass quality ratings for 'Patriot' and eight other cultivars in the 1997 National Turfgrass Evaluation Program bermudagrass test.

| Seeded Cultivars | | | | |
|---|---|---|---|---|
| Arizona Common | 4.6 | 28 | 539 | 28 |
| Blackjack | 5.2 | 17 | 343 | 18 |
| Blue-Muda | 5.0 | 24 | 433 | 25 |
| J-540 | 5.2 | 18 | 353 | 19 |
| Jackpot | 4.9 | 26 | 470 | 27 |
| Majestic | 5.2 | 19 | 340 | 17 |
| Mirage | 5.0 | 25 | 425 | 24 |
| Numex-Sahara | 4.9 | 27 | 469 | 26 |
| Princess | 6.3 | 5 | 121 | 3 |
| Pyramid | 5.0 | 23 | 416 | 23 |
| Riviera | 6.5 | 1 | 91 | 1 |
| Savannah | 5.3 | 15 | 317 | 14 |
| ShangriLa | 5.1 | 21 | 409 | 22 |
| Southern Star | 5.3 | 16 | 335 | 16 |
| Sundevil II | 5.1 | 22 | 394 | 21 |
| SWI-11 | 5.8 | 11 | 234 | 12 |
| Sydney | 5.2 | 20 | 385 | 20 |
| Transcontinental | 5.7 | 12 | 215 | 11 |

| | Statistics for all locations | | |
|---|---|---|---|
| | Highest Rank[5] | Lowest Rank[6] | Maximum in Top 25%[7] |
| Clonal Cultivars | | | |
| Cardinal | 1 | 28 | 20 |
| CN 2-9 | 2 | 25 | 25 |
| Midlawn | 1 | 27 | 60 |
| Mini-Verde | 5 | 28 | 30 |
| Patriot | 1 | 11 | 65 |
| Shanghai | 3 | 16 | 30 |
| Tifgreen | 1 | 22 | 70 |
| Tifsport | 1 | 20 | 60 |
| Tifway | 1 | 23 | 75 |
| Seeded Cultivars | | | |
| Arizona Common | 23 | 28 | 0 |
| Blackjack | 4 | 27 | 5 |
| Blue-Muda | 5 | 26 | 5 |
| J-540 | 12 | 24 | 0 |
| Jackpot | 16 | 28 | 0 |
| Majestic | 13 | 26 | 0 |
| Mirage | 7 | 28 | 5 |
| Numex-Sahara | 16 | 27 | 0 |
| Princess | 1 | 12 | 60 |
| Pyramid | 9 | 27 | 0 |
| Riviera | 1 | 12 | 80 |
| Savannah | 12 | 23 | 0 |
| ShangriLa | 10 | 27 | 0 |
| Southern Star | 11 | 28 | 0 |
| Sundevil II | 13 | 28 | 0 |
| SWI-11 | 2 | 20 | 25 |
| Sydney | 6 | 28 | 5 |
| Transcontinental | 3 | 21 | 20 |

[1]Mean—An average of all the turfgrass quality ratings from all locations.
[2]Rank—Ranking of the mean of all quality ratings.
[3]Sum of ranks—a sum of all the rankings from the various locations.
[4]Rank—The ranking of the sum of ranks.
[5]Highest rank—The highest ranking achieved by that entry at any one location.
[6]Lowest rank—The lowest ranking achieved by that entry at any one location.
[7]Maximum in top 25%—The percentage of locations where that entry finished in the top 25% of all entries.

TABLE 3

Mean genetic color ratings of 'Patriot' and eight other bermudagrass cultivars in the 1997 National Turf Evaluation Program bermudagrass test.[1]

| Cultivar | Rating[2] |
|---|---|
| Cardinal | 4.7 |
| CN 2-9 | 7.2 |
| Midlawn | 6.5 |
| Mini-Verde | 6.7 |
| Patriot | 7.4 |
| Shanghi | 7.5 |
| Tifgreen | 6.2 |
| Tifsport | 7.0 |
| Tifway | 7.1 |
| 5% LSD | 0.2 |
| CV (%) | 14.4 |

[1]Means over 21 locations and 5 years (1997–2001).
[2]Based on a visual rating scale with 1 being light green and 9 being dark green.

TABLE 4

Mean leaf texture ratings of 'Patriot' and eight other bermudagrass cultivars in the 1997 National Turf Evaluation Program bermudagrass test.[1]

| Cultivar | Rating[2] |
|---|---|
| Cardinal | 8.2 |
| CN 2-9 | 6.9 |
| Midlawn | 6.9 |
| Mini-Verde | 8.2 |
| Patriot | 6.7 |
| Shanghai | 5.1 |
| Tifgreen | 7.7 |
| Tifsport | 7.2 |
| Tifway | 7.3 |
| 5% LSD | 0.2 |
| CV (%) | 14.4 |

[1]Means over 20 locations and 5 years (1997–2001).
[2]An estimate of leaf width based on a visual rating scale with 1 equaling coarse and 9 equaling fine.

TABLE 5

Mean stand density ratings of 'Patriot' and eight other bermudagrass cultivars in the 1997 National Turf Evaluation Program bermudagrass test.[1]

| | Stand density rating[2] | | |
|---|---|---|---|
| Cultivar | Spring | Summer | Fall |
| Cardinal | 7.6 | 7.3 | 7.4 |
| CN 2-9 | 6.5 | 7.1 | 7.0 |
| Midlawn | 7.1 | 7.1 | 7.1 |
| Mini-Verde | 6.9 | 8.1 | 7.8 |
| Patriot | 6.7 | 7.5 | 7.2 |
| Shanghai | 6.2 | 6.8 | 6.4 |
| Tifgreen | 7.3 | 7.6 | 7.5 |
| Tifsport | 7.2 | 7.6 | 7.6 |
| Tifway | 7.3 | 7.7 | 7.6 |
| 5% LSD | 0.4 | 0.3 | 0.3 |
| CV (%) | 18.1 | 12.3 | 13.8 |

[1]Means over 9 locations and 5 years (1997–2001).
[2]An estimate of living plants or tillers per unit area based on a visual rating scale with 9 equaling maximum density.

TABLE 6

Mean percent living ground cover ratings of 'Patriot' and eight other bermudagrass cultivars in the 1997 National Turf Evaluation Program bermudagrass test.[1]

| | Ground cover rating[1] | | |
|---|---|---|---|
| Cultivar | Spring[2] | Summer[3] | Fall[4] |
| Cardinal | 87.0 | 89.9 | 86.7 |
| CN 2-9 | 70.1 | 88.3 | 91.6 |
| Midlawn | 85.9 | 90.8 | 88.2 |
| Mini-Verde | 59.3 | 78.8 | 87.7 |
| Patriot | 84.0 | 90.7 | 90.0 |
| Shanghai | 77.8 | 87.3 | 87.6 |
| Tifgreen | 78.7 | 91.4 | 91.0 |
| Tifsport | 71.4 | 89.5 | 93.9 |
| Tifway | 76.8 | 91.4 | 93.7 |
| 5% LSD | 5.5 | 3.8 | 4.0 |
| CV (%) | 24.8 | 14.0 | 12.1 |

[1]Percent living ground cover based on surface area covered by the originally planted species.
[2]Means over 14 locations and 5 years.
[3]Means over 9 locations and 5 years.
[4]Means over 8 locations and 5 years.

TABLE 7

Mean winter injury ratings of 'Patriot' and eight other bermudagrass cultivars in the 1997 National Turf Evaluation Program bermudagrass test at Wichita, KS in 2001.

| Cultivar | Rating |
|---|---|
| Cardinal | 5.0 |
| CN 2-9 | 2.3 |
| Midlawn | 5.7 |
| Mini-Verde | 3.0 |
| Patriot | 6.7 |
| Shanghai | 5.3 |
| Tifgreen | 4.0 |
| Tifsport | 3.7 |
| Tifway | 2.7 |
| 5% LSD | 2.3 |
| CV (%) | 32.7 |

[1]Injury due to low winter temperatures based on a rating scale with 1 indicating severe injury and 9 indicating no injury.

TABLE 8

Freeze tolerance of 'Patriot' and six other turf bermudagrass cultivars. $T_{mid}$ values represent the midpoints of survival-temperature response curves[1].

| Cultivar | $T_{mid}$ ° C. |
|---|---|
| Princess | −6.9a[†] |
| Tifway | −7.9b |
| Tifsport | −7.9b |
| Riviera | −8.3bc |
| U-3 | −8.9cd |
| Patriot | −9.7de |
| Midlawn | −10.3e |

[1]Jeffrey A. Anderson et al. 2003. Longer exposure durations increase freeze damage to turf bermudagrass. Crop Sci. 43:973–977.
[†]Means of four repetitions are separated by Duncan's New Multiple Range Test at P,0.05.

TABLE 9

Mean establishment measurements or ratings of Patriot and eight other bermudagrass cultivars in the 1997 National Turf Evaluation Program bermudagrass test.[1] 1997 Measurements by date or weeks after planting.

| | Fayetteville, AR | Griffin, GA | | | Lexington, KY |
|---|---|---|---|---|---|
| Cultivar | September | 2 Wks | 4 Wks | 6 Wks | 3 Wks |
| Cardinal | 88.3 | 28.3 | 68.3 | 91.0 | 51.3 |
| CN 2-9 | 60.0 | 26.7 | 58.3 | 81.7 | 33.3 |
| Midlawn | 86.7 | 26.7 | 60.0 | 81.7 | 46.0 |
| Mini-Verde | 53.3 | 26.7 | 58.3 | 71.7 | 36.7 |
| Patriot | 93.0 | 33.3 | 70.0 | 97.7 | 56.0 |
| Shanghai | 95.0 | 38.3 | 71.7 | 95.0 | 50.3 |
| Tifgreen | 90.0 | 28.3 | 66.7 | 90.0 | 48.3 |
| Tifsport | 63.3 | 18.3 | 53.3 | 71.7 | 34.3 |
| Tifway | 71.7 | 26.7 | 58.3 | 76.7 | 29.3 |
| 5% LSD | 15.7 | 11.0 | 10.1 | 10.0 | 11.5 |
| CV (%) | 12.4 | 19.4 | 8.7 | 7.1 | 16.6 |

| | Lexington, KY | | Starkville, MS | |
|---|---|---|---|---|
| Cultivar | 5 Wks | 13 Wks | 4 Wks | 6 Wks |
| Cardinal | 94.0 | 99.0 | 58.3 | 93.0 |
| CN 2-9 | 77.7 | 99.0 | 50.0 | 81.7 |
| Midlawn | 93.3 | 99.0 | 58.3 | 93.0 |
| Mini-Verde | 80.0 | 98.3 | 41.7 | 81.7 |
| Patriot | 95.3 | 99.0 | 71.7 | 96.0 |
| Shanghai | 96.3 | 99.0 | 76.7 | 94.7 |
| Tifgreen | 92.3 | 99.0 | 66.7 | 96.3 |
| Tifsport | 68.3 | 97.3 | 53.3 | 83.3 |
| Tifway | 75.0 | 98.7 | 45.0 | 78.3 |
| 5% LSD | 9.4 | 1.2 | 12.0 | 10.8 |
| CV (%) | 6.8 | 0.7 | 12.9 | 6.8 |

TABLE 9a

Mean seedhead ratings of 'Patriot' and eight other bermudagrass cultivars in the 1997 National Turf Evaluation Program bermudagrass test.[1]

| Cultivar | Riverside, CA, 1999 | | Stillwater, OK, 1999 | | |
|---|---|---|---|---|---|
| Cardinal | 8.0 | 4.0 | 8.0 | 8.0 | 8.0 |
| CN 2-9 | 8.7 | 8.0 | 8.7 | 7.7 | 9.0 |
| Midlawn | 8.7 | 5.3 | 9.0 | 8.0 | 9.0 |
| Mini-Verde | 9.0 | 8.7 | 9.0 | 9.0 | 9.0 |
| Patriot | 9.0 | 7.7 | 9.0 | 8.0 | 8.3 |
| Shanghai | 9.0 | 7.3 | 8.7 | 8.0 | 9.0 |
| Tifgreen | 9.0 | 6.0 | 8.3 | 7.3 | 9.0 |
| Tifsport | 8.7 | 7.3 | 8.7 | 8.0 | 9.0 |
| Tifway | 8.3 | 8.0 | 8.7 | 8.0 | 9.0 |
| 5% LSD | 0.9 | 1.0 | 0.7 | 0.4 | 0.3 |
| CV (%) | 4.8 | 9.0 | 4.4 | 3.1 | 2.1 |

[1]Ratings of seedhead abundance on a scale of 1 to 9 with 9 indicating none.

TABLE 10

Mean spring dead spot necrotic patch area ($cm^2$) of bermudagrass cultivars in the 1997 National Turf Evaluation Program Bermudagrass Trial[1] at Stillwater, OK. Plots were inoculated with a blend of *Ophiosphaerella herpotricha* isolates KS107, KS112 and KS188 in September 1997.

| Entry | 2000 | 2001 | 2002 |
|---|---|---|---|
| Arizona Common | 622 | 1791 | 2221 |
| Cardinal | 25 | 28 | 76 |
| CN-2-9 | 383 | 931 | 1904 |
| Continental | 806 | 2124 | 3178 |

TABLE 10-continued

Mean spring dead spot necrotic patch area ($cm^2$) of bermudagrass cultivars in the 1997 National Turf Evaluation Program Bermudagrass Trial[1] at Stillwater, OK. Plots were inoculated with a blend of *Ophiosphaerella herpotricha* isolates KS107, KS112 and KS188 in September 1997.

| Entry | 2000 | 2001 | 2002 |
|---|---|---|---|
| Blackjack | 751 | 1372 | 2035 |
| Blue Muda | 806 | 1835 | 2377 |
| GN-1 | 1367 | 1722 | 1410 |
| Jackpot | 682 | 1805 | 2293 |
| J-540 | 876 | 2333 | 2180 |
| Majestic | 1081 | 2531 | 3096 |
| Midlawn | 20 | 45 | 99 |
| Mini-Verde | 1195 | 3677 | 4902 |
| Mirage | 747 | 1626 | 1923 |
| OKC 19-9 | 68 | 133 | 429 |
| Patriot (OKC 18-4) | 377 | 754 | 766 |
| Princess 77 | 1947 | 3727 | 3312 |
| Pyramid | 1093 | 2417 | 2886 |
| Riviera (OKS 95-1) | 795 | 1116 | 1595 |
| Sahara | 618 | 1734 | 2416 |
| Savannah | 717 | 1731 | 2186 |
| Shanghai | 779 | 1207 | 1277 |
| Shangri La | 742 | 1760 | 2476 |
| Southern Star | 809 | 1753 | 2263 |
| Sundevil II | 637 | 1555 | 2289 |
| SW1-11 | 537 | 2184 | 2589 |
| Sydney | 834 | 1257 | 2642 |
| Tifgreen | 486 | 1118 | 2125 |
| Tifsport | 473 | 927 | 996 |
| Tifway | 469 | 1133 | 2754 |
| Yukon (OKS 91-11) | 167 | 345 | 678 |
| LSD (0.05) | 698 | 1096 | 678 |

[1]Yukon and GN-1 were included at the Stillwater, OK, NTEP Bermudagrass Test Site as local standards.

SEQUENCE LISTING

```
<160> NUMBER OF SEQ ID NOS: 1

<210> SEQ ID NO 1
<211> LENGTH: 8
<212> TYPE: DNA
<213> ORGANISM: Artificial
<220> FEATURE:
<223> OTHER INFORMATION: oligonucleotide primer

<400> SEQUENCE: 1

gaaacgcc                                                          8
```

What is claimed is:

1. A bermudagrass plant substantially as described and illustrated in the specification herein.

* * * * *